(12) United States Patent
Stern (10) Patent No.: US 8,460,310 B2
(45) Date of Patent: Jun. 11, 2013

(54) SURGICAL BASE UNIT AND RETRACTOR SUPPORT MECHANISM

(76) Inventor: Leslie Stern, Fall River, MA (US)

( * ) Notice: Subject to any disclaimer, the term of this patent is extended or adjusted under 35 U.S.C. 154(b) by 799 days.

(21) Appl. No.: 12/618,916

(22) Filed: Nov. 16, 2009

(65) Prior Publication Data

US 2010/0076447 A1 Mar. 25, 2010

Related U.S. Application Data

(63) Continuation-in-part of application No. 11/098,770, filed on Apr. 4, 2005, now Pat. No. 7,637,914.

(60) Provisional application No. 60/598,739, filed on Aug. 4, 2004.

(51) Int. Cl.
*A61B 17/70* (2006.01)

(52) U.S. Cl.
USPC ............................. 606/105; 606/86 A; 606/99

(58) Field of Classification Search
USPC ............... 606/57, 60, 86 R, 90–99, 205–208, 606/246, 279, 86 A, 104, 105; 600/213, 215, 600/227–231, 234, 235, 210
See application file for complete search history.

(56) References Cited

U.S. PATENT DOCUMENTS

| | | | | |
|---|---|---|---|---|
| 4,733,657 A | * | 3/1988 | Kluger | 606/57 |
| 5,219,349 A | * | 6/1993 | Krag et al. | 606/53 |
| 5,797,963 A | | 8/1998 | McDevitt | 606/232 |
| 6,126,660 A | | 10/2000 | Dietz | 606/61 |
| 6,648,888 B1 | | 11/2003 | Shluzas | 606/61 |
| 6,749,613 B1 | | 6/2004 | Conchy et al. | 606/61 |
| 7,160,300 B2 | * | 1/2007 | Jackson | 606/273 |
| 2003/0167059 A1 | | 9/2003 | Young | 606/61 |
| 2003/0187436 A1 | | 10/2003 | Bolger et al. | 606/61 |
| 2004/0039384 A1 | | 2/2004 | Boehm, Jr. et al. | 606/61 |
| 2004/0138662 A1 | | 7/2004 | Landry et al. | 606/61 |

(Continued)

FOREIGN PATENT DOCUMENTS

| | | |
|---|---|---|
| WO | WO 00/48523 | 8/2000 |
| WO | WO 03/024344 | 3/2003 |
| WO | WO 2004/047650 | 6/2004 |

OTHER PUBLICATIONS

Website: Spinal Concepts-Path Finder™; http://www.spinalconcepts.com/products/pathfinder.htm; 2004, [retrieved on Jul. 7, 2005].
Website: Spine-Health.com; http://www.spine-health.com/topics/surg/mini/mimimally-invasive.02.html.; pp. 1-2, [retrieved on Jul. 7, 2005].

*Primary Examiner* — Eduardo C Robert
*Assistant Examiner* — Tara Carter
(74) *Attorney, Agent, or Firm* — Sunstein Kann Murphy & Timbers LLP (57) ABSTRACT

An apparatus and methods for exerting force on a first bone with respect to a fulcrum, which may be a second bone. A base structure, mechanically coupled to the fulcrum, is coupled to the closure top so that a force may be exerted by the base structure, acting against the fulcrum, in at least one of axial and transverse directions with respect to a pedicle screw inserted into bone. A leg extension, allowing force to be applied through the pedicle screw to a bone, has a first end rotatably coupled to the base structure; and a second end threaded as the closure top. The base structure may also support a retractor in a manner local to the immediate region of surgery.

16 Claims, 10 Drawing Sheets

U.S. PATENT DOCUMENTS

| | | | |
|---|---|---|---|
| 2005/0021040 A1 | 1/2005 | Bertagnoli | 606/90 |
| 2005/0059972 A1 | 3/2005 | Biscup | 606/73 |
| 2005/0085813 A1 | 4/2005 | Spitler et al. | 606/61 |
| 2005/0216000 A1 | 9/2005 | Colleran et al. | 606/61 |
| 2005/0245928 A1 | 11/2005 | Colleran et al. | 606/61 |
| 2006/0036240 A1 | 2/2006 | Colleran et al. | 606/61 |
| 2006/0036244 A1 | 2/2006 | Spitler et al. | 606/61 |
| 2006/0079894 A1 | 4/2006 | Colleran et al. | 606/61 |
| 2006/0106380 A1 | 5/2006 | Colleran et al. | 606/61 |
| 2006/0106394 A1 | 5/2006 | Colleran | 606/86 |
| 2006/0173454 A1 | 8/2006 | Spitler et al. | 606/61 |

* cited by examiner

SURGICAL BASE UNIT AND RETRACTOR SUPPORT MECHANISM

The present application is a continuation-in-part application of U.S. Ser. No. 11/098,770, filed Apr. 4, 2005 and issued as U.S. Pat. No. 7,637,914, and, like that application, claims priority from U.S. Provisional Application Ser. No. 60/598,739, filed Aug. 4, 2004. Both of the foregoing patent applications are incorporated herein by reference.

TECHNICAL FIELD

The present invention pertains to devices and methods for locally securing a support base at the site of an incision by anchoring to a pedicle screw inserted into one or more bones, which support base may be used for exerting relative forces on the bones as well as for supporting a further surgical retractor.

BACKGROUND ART

Fusion of lumbar vertebrae is performed under circumstances including those in which degenerative disk disease, scoliosis, or other deformity indicates that stopping motion between adjacent vertebral segments is desirable. The fusion procedure entails inserting a bone graft between vertebral elements thereby inducing bone growth that ultimately fuses the adjoining vertebral elements. In order to accomplish the fusion of lumbar vertebrae in a minimally invasive manner, procedures, such as those performed in accordance with the Pathfinder™ System of Abbott Spine of Austin, Tex., provide for insertion and retention of a stabilizing rod between pedicle screws, one of which is anchored into each of the adjoining vertebrae, so as to maintain them at a fixed relative displacement after the graft has been inserted and until the biological response completes the fusion process.

It should be noted that lumbar fusion surgery may require relative positioning of adjacent vertebrae in various planes, whether by relative distraction or compression of the intervertebral space, or by reduction, i.e., displacement of a vertebra in a plane transverse to the axis of the spine, i.e., in a direction that will be referred to herein as 'vertical,' as referred to a prone patient.

Figure 1:
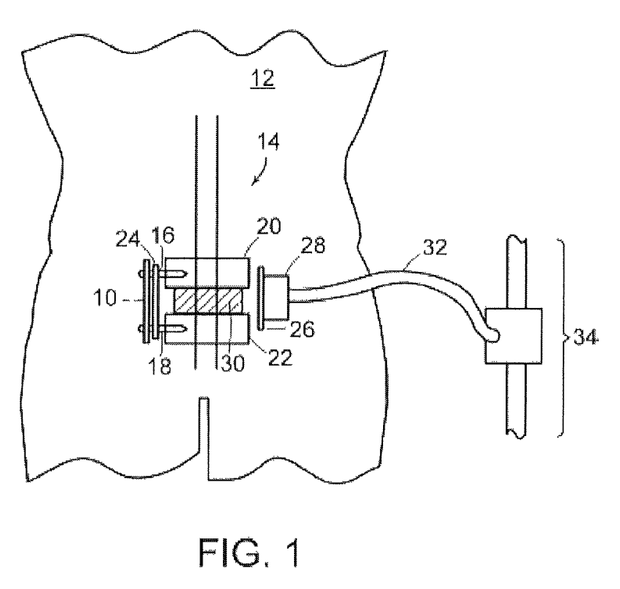
FIG. 1 depicts fundamental features of lumbar fusion surgery in accordance with prior art methods showing a retractor fixed to the operating table.

Using minimally invasive surgical procedures, lumbar fusion surgery is begun as now described with reference to FIG. 1. A first incision 10 is performed in the patient's back 12, parallel to the spine 14 and to one side. Though this incision, pedicle screws 16 and 18 are inserted, by known procedures, into the pedicles of adjoining vertebrae 20 and 22, such as lumbar vertebrae L4 and L5. Rod 24 is inserted through slotted guides attached to the heads of pedicle screws 16 and 18 and secured with respect to each of the pedicle screws by closure tops, typically set screws that are threaded for retention in a corresponding helical thread of the pedicle screws. In order to drive the closure tops into the pedicle screws to tighten a transverse rod, a surgeon, using existing systems, typically employs specialized tools that engage the closure tops by means of a slotted or socket driver.

The rest of the lumbar fusion procedure proceeds via a second incision 26 made parallel to the first incision 10 and laterally opposite to the first incision on the other side of the spine. The soft tissues of the second incision are held apart by a retractor 28 so that a graft 30 may be inserted between vertebrae 20 and 22. A retractor typically serves to hold the soft tissues of the surgical incision while the surgeon operates on exposed elements of the spinal column. Retractor 28 is typically tethered, via flexible arm 32, to a mounting 34 fixed with respect to the operating table. This method of mounting retractor 28 is unwieldy and subject to a potential breach of sterility while accessing the surgical site.

It is desirable for reasons both of convenience and sterility that a method and apparatus be provided whereby forces may be applied to a bone, such as a vertebra, with respect to a local fulcrum, and also that a method and apparatus be provided for supporting a retractor 28 locally to the region of the surgery.

SUMMARY OF THE INVENTION

In accordance with preferred embodiments of the present invention, an apparatus is provided for exerting force on a bone with respect to a fulcrum. The apparatus has a base structure, mechanically coupled to the fulcrum, and a leg extension coupled to the base structure via a rotatable coupling. The leg extension, in turn, is adapted for coupling to a closure top threaded for retention in a corresponding helical thread of a pedicle screw, such that rotation of the leg extension urges the closure top into the helical thread of the pedicle screw.

In accordance with alternate embodiments of the present invention, the base structure may also have a simple machine adapted to urge the leg extension in both axial and transverse directions with respect to the pedicle screw axis. The simple machine may be adapted to urge the leg extension simultaneously in both axial and transverse directions with respect to the pedicle screw axis, or to urge the leg extension sequentially in both axial and transverse directions with respect to the pedicle screw axis. The simple machine may be a toothed ratchet drive or a worm drive. In yet further embodiments of the invention, the simple machine may be adapted to urge the leg extension in either axial or transverse directions with respect to the pedicle screw axis.

In accordance with other embodiments of the present invention, the leg extension and the closure top may constitute an integral component. The leg extension may be frangibly coupled to the closure top. Additionally, a retractor may be coupled to the base structure, and the retractor may be coupled by a flexible arm.

In accordance with another aspect of the present invention, a leg extension is provided for coupling a pedicle screw to a base structure. The leg extension enables force to be applied through the pedicle screw to a bone. The leg extension has a first end adapted for rotatable coupling with respect to the base structure and a second end threaded for retention in a corresponding helical thread of the pedicle screw.

In other embodiments, the leg extension may be integral with a closure top, and the leg extension and closure top may be frangibly coupled. The first end of the leg extension may be further adapted for rotatable coupling to the base structure by means of a snap-lock joint, and may also have a through-hole transverse to the central axis of the leg extension for receiving a torque pin for application of torque about the central axis.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

In accordance with preferred embodiments of the present invention, forces may be applied to a bone with respect to an effectively fixed fulcrum, or between adjacent bones, by a trestle-structure base unit designated generally by numeral 200, as now described with reference to FIG. 2A. Base unit 200 may function alone, or in conjunction with a retractor 500 (shown in FIG. 5) supported by the base unit. The purpose of retractor 500, namely, for holding the edge of a surgical incision, has been discussed above.

Figure 5:
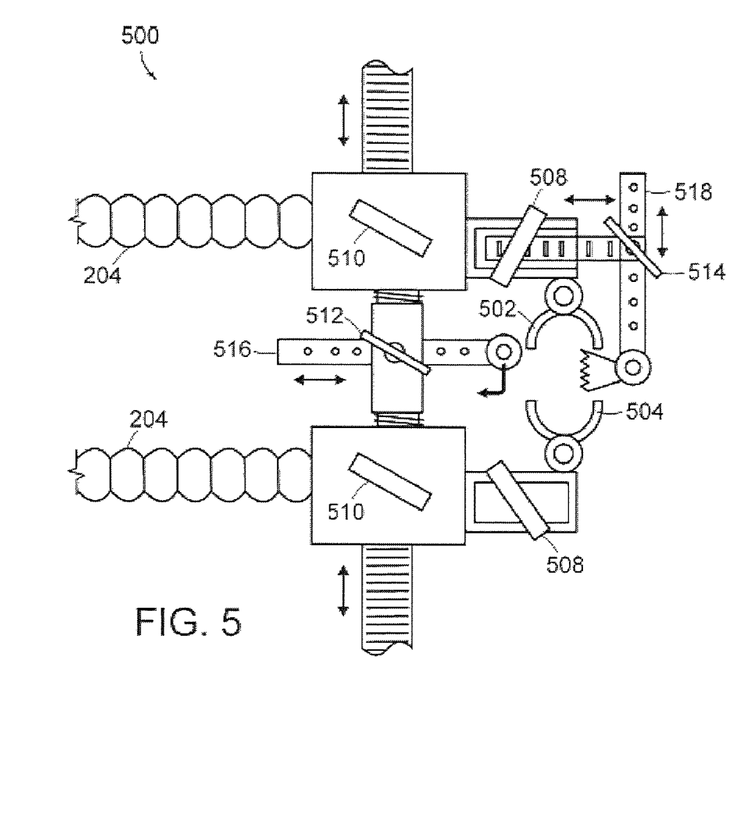
FIG. 5 is a top view of a retractor for minimally invasive surgery as coupled to the base unit of FIG. 2 in accordance with an embodiment of the present invention.

Base unit 200 has two legs (or "posts") 202, each of which is coupled, as described in further detail below, to a pedicle screw 16, 18, anchored to the skeletal system of the patient. Trestle base unit 200 may also serve to support one or more flexible arms 204 to which, in turn, the retractor 500 of FIG. 5 is coupled. Leg extensions 219 are coupled to legs 202, typically via rotating coupling 240, as further discussed, below, with reference to FIG. 2B. It should be noted that base unit 200 may also be referred to, herein, as a "retractor support structure," or "retractor support," in that, in certain embodiments of the invention, the base unit also serves to provide local support for retractor 500, in a manner that is independent of any structure fixed with respect to the operating table.

Figure 3A:
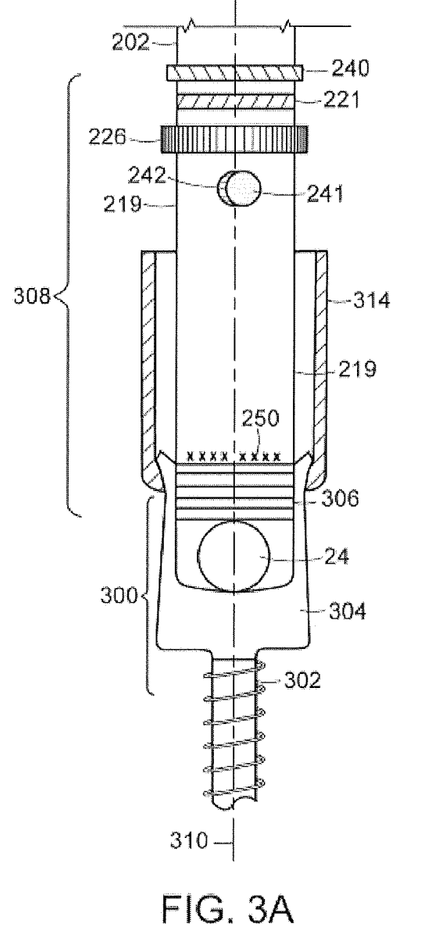
FIG. 3A is a cross section of an elongated closure top supporting a retractor leg in relation to a pedicle screw in accordance with preferred embodiments of the present invention.

Support of legs 202 of base unit 200 with respect to the pedicle screws is described, now, with reference to FIG. 3A, in which a pedicle screw is designated generally by numeral 300. The application of forces between the components of the base unit will be described below. Pedicle screw 300 is retained within the pedicle by means of threads 302 at the distal end of the screw. A pedicle screw 300 may be retained, for example, in the sacrum, in cases where the L5 vertebral body has "slipped" with respect to the sacrum. Pedicle screw body 304 is notched to receive a rod 24, seen here from the end, with the axis of rod 24 directed into the plane of the page. Rod 24, once secured with respect to two pedicle screws, maintains a fixed separation between adjoining vertebrae so that a graft may be inserted between them, and, further, stabilizes the vertebrae until the graft has resulted in fusion of the two vertebrae. Rod 24 is secured with respect to pedicle screw 300 by advancing threaded end 306 of closure top assembly 308 into the correspondingly threaded central socket of pedicle screw body 304.

In the embodiment of the invention depicted in FIG. 3A, closure top assembly 308 is an integral assembly with leg extension 219, the combination comprising a disposable element of the apparatus, and forces may be applied by base unit 200 to a bone, via pedicle screw 304, as described below. After the surgical procedure has been completed, leg extension 219 may be sheared off from threaded end 306 of closure top assembly 308 at breakpoint 250. Alternately, closure top assembly 308 may be withdrawn after the procedure has been completed, and may be replaced with a standard closure top in order to retain rod 24.

Closure top assembly 308 is advanced into pedicle screw body 304 by applying a torque to closure top assembly 308 about central axis 310. In one embodiment of the invention, torque may be applied to closure top assembly 308 by means of a torque pin (or "torque wrench") 241, inserted into through-hole 242, as shown, in its inserted position, in FIG. 3C, or by means of knurled grip 226. In the former embodiment, torque pin 241 facilitates the rotation of leg extension 219 about its axis at radial joint 240, as further discussed below. A front view of the pedicle screw/retractor leg extension assembly is depicted in FIG. 3D.

Figure 3B:
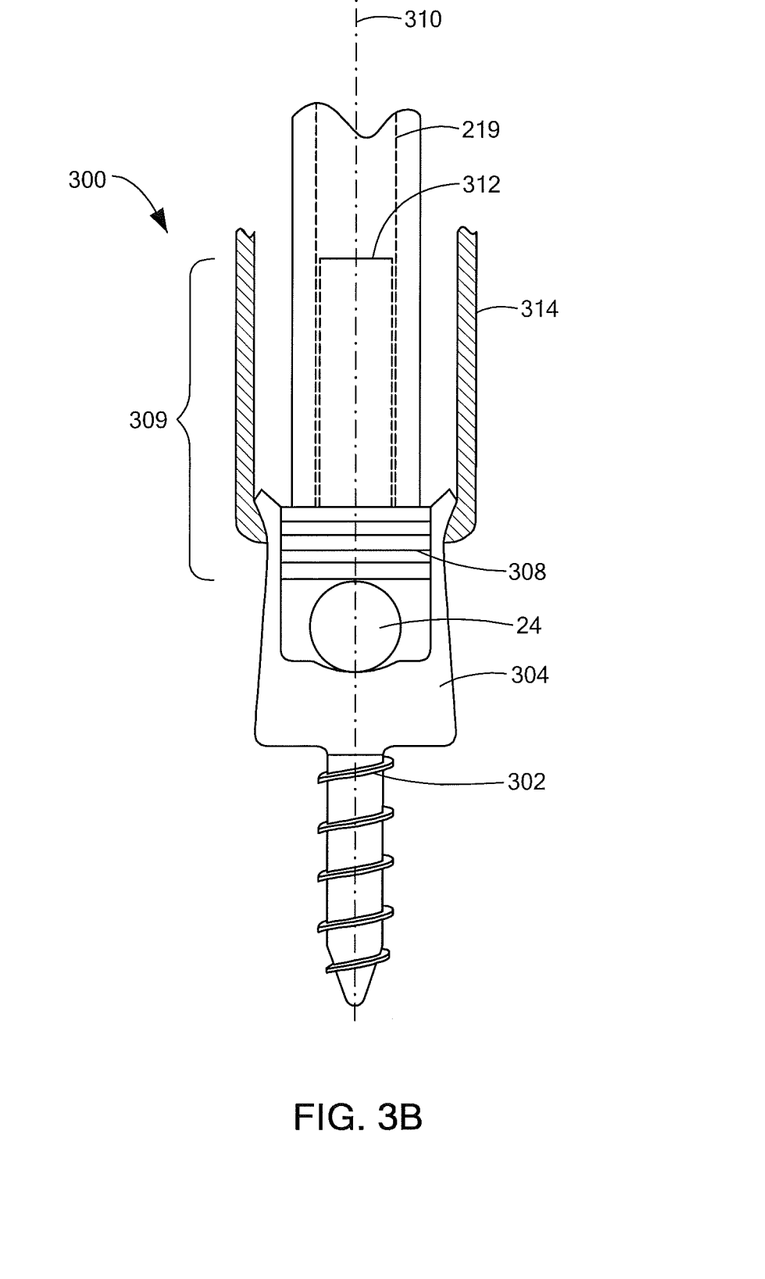
FIG. 3B is a cross section of the elongated closure top of FIG. 3A, through a different rotation angle of the closure top about its longitudinal axis. so as to show the extended shank of the closure top in accordance with preferred embodiments of the present invention.
Figure 3C:
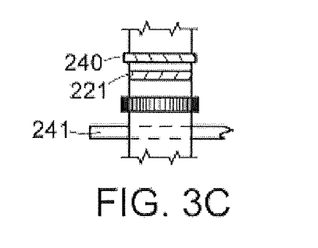
FIG. 3C shows the insertion of a torque pin into retractor leg extension of FIG. 3A.
Figure 3D:
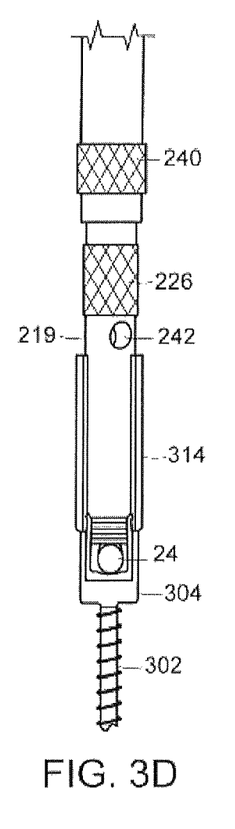
FIG. 3D is a front view of the pedicle screw/retractor leg assembly.

Torque may be exerted through an extended shank 312 that is shown in FIG. 3B by application of a tool (such as a socket wrench, or leg extension 219) that has an internal cavity of cross section matching the cross section of the extended shank. Such a tool captures shank 312, which is the extension of threaded portion 306 of a closure top designated in FIG. 3B by numeral 309. However, to the extent to which such tools fail to capture the closure top, only torque may be applied, while forces parallel to the pedicle screw axis 310 may not be applied. Shank 312, in this case, is characterized by a cross section preferably shaped to facilitate application of torque to the closure top, thus the cross section may be that of a regular polygon, such as a pentagon or hexagon. It is to be understood that the invention is not limited with respect to the means provided for applying torque to drive closure top 309 into pedicle screw 300. For example, shank 312 may also have an interior slot by means of which it is driven with a tool into pedicle screw 300.

Figures 2A, 2G:
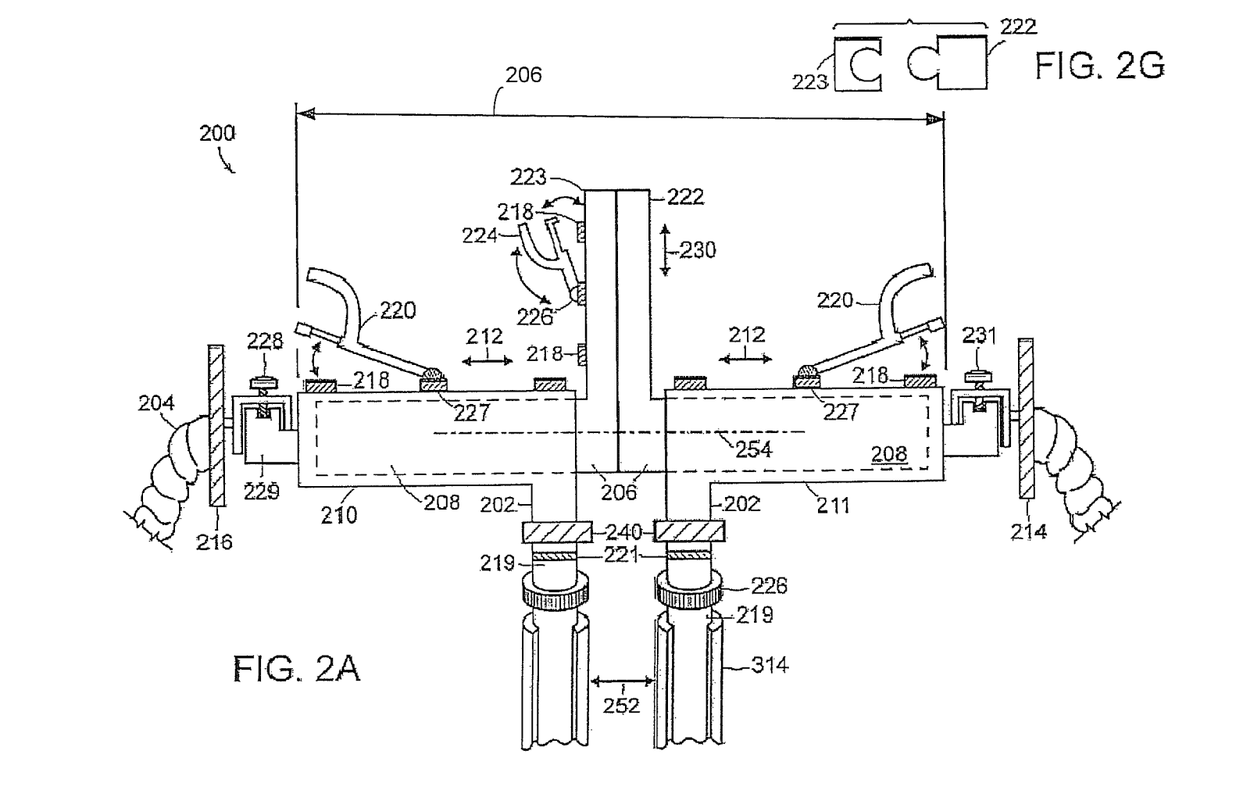
FIG. 2A shows a support base unit including a support trestle and abutting L segments for applying both axial and vertical forces between pedicle screws anchored in adjoining vertebrae in accordance with preferred embodiments of the present invention.
FIG. 2G is a top view of the upright portions of the base unit, showing their interlocking groove structure, in accordance with certain embodiments of the present invention.

In accordance with alternate embodiments of the present invention such as the embodiment depicted in FIG. 3B, extended shank 312 of closure top 309 may serve not only for advancing the closure top so as to secure rod 24 but also as a base on which to support leg 202 (or, in yet other embodiments of the invention, an extension 219 thereof) of retractor support structure 200 (shown in FIG. 2A). Leg extension 219 is tubular, containing an interior cavity inserted over, and thereby engaged with, shank, 312. The cross section of the interior cavity of leg extension 219 may be shaped to mate with the exterior cross section of shank 312. Alternatively, while not a favored embodiment of the invention, it is to be understood that the cross section of interior cavity may also circumscribe the exterior cross section of shank 312 so that the orientation of retractor support structure 200 is not constrained with respect to rotation about axis 310. Leg extension 219, in that embodiment, is inserted over shank 312 and within an extender sleeve 314 of pedicle screw 300, however a separate socket wrench would then typically be used to urge closure top 309 into pedicle screw 300.

Returning now to description of the embodiment depicted in FIG. 3A, leg extension 219 is coupled to support leg 202 by rotational coupling 240 that provides for rotation of leg extension 219 about its longitudinal axis, so that it may be rotated about axis 310, thereby providing torque to closure top assembly 308 for insertion into pedicle screw 300.

Support of legs 202 of retractor support structure 200 by means of closure tops 308 having been described, retractor support 200 is now further described with reference to FIG. 2A. Legs 202 of retractor support 200 are traversed by a cross-bar, designated generally by numeral 206. In accordance with preferred embodiments of the invention, cross-bar 206 has a left sleeve section 210 and a right sleeve section 211, capable of telescoping adjustment with respect to one another so that the length 200 of cross-bar 206 may be adjusted along direction 212 so as to obtain a desired spacing 252 between legs 202 to match the spacing between centers of pedicle screws 300 after attachment to adjacent vertebrae. Adjustment of the length of cross-bar 206 may use any convenient mechanism known in the art. Ratchet handles 220 are used to actuate ratchet mechanisms 227, acting to provide sequential separation of cross-bar sleeve sections 210 and 211 by urging each with respect to inner sections 208, and thereby providing distraction or compression of the bones retaining the pedicle screws to which support legs 202 are attached.

Legs 202, and thus also leg extensions 219, are maintained in perpendicular alignment with respect to crossbar 206 in the manner depicted and heretofore described. Since crossbar 206 is substantially horizontal, and thus substantially parallel to the longitudinal axis of spine 14 of a prone surgical patient, legs 202 and leg extensions 219 are elements that are maintained in parallel alignment, and, during the course of surgery, they are maintained substantially upright. Ratchet mechanisms 227 may include a toothed ratchet drive that engages teeth in the inner sections 208. Ratchet levers 220 are locked to pedestals 218 for securing sleeve sections 210 and 211 at a determined relative disposition, once set by adjustment of ratchet mechanisms 227. Other means known in the mechanical arts for adjusting the separation of sleeve sections 210 and 211 (such as a worm drive, for example, or any other simple machine), and of securing them at a determined relative disposition, are similarly within the scope of the present invention. By operation of the mechanisms heretofore described, forces are applied, through each leg extension 219, to a bone, more particularly, a vertebra, in directions that are axial or transverse with respect to pedicle screw 300, or, at the surgeon's discretion, in both directions at the same time. Forces may be applied in the axial and transverse directions either in sequence or simultaneously.

Figure 2B:
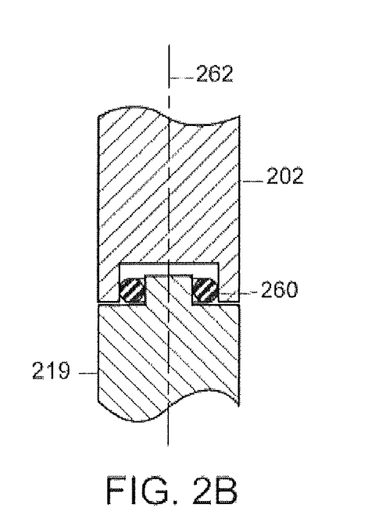
FIGS. 2B-2D show alternate embodiments of the coupling between the support leg of the support base unit and a rotatable leg extension, in accordance with representative embodiments of the present invention.

A further embodiment of base structure 200, in accordance with the present invention, is depicted in FIG. 21. Elements of the base structure are designated by numerals identified with reference to drawings that have been described above.

In the embodiment of the invention depicted in FIG. 2A, inner transverse sections 208 are the horizontal legs of L-shaped members of which uprights 222 and 223 form the corresponding vertical legs. Uprights 222 and 223 preferably slide with respect to one another while retained in relative alignment by means of the tongue-in-groove configuration shown in the top view of FIG. 2G. Thus, the uprights 222 and 223 may be separated for sterilization purposes. Ratchet mechanism 227, activated by lever 224, acts to urge uprights 222 and 223 in relative vertical displacement, thereby exerting vertical forces, through legs 202, leg extensions 219, and pedicle screws 300, to reduce misalignment in the vertical plane of the bones to which the pedicle screws are attached. For example, misalignment of the spine (listhesis) may be reduced by elevation of a vertebra with respect to a caudal vertebra and/or the sacrum as a fulcrum.

Sleeve sections 210 and 211 are coupled to legs 202 as further described below with reference to FIG. 2A. In preferred embodiments of the invention, leg 202 is coupled to leg extension 219 (which, in preferred embodiments, is part of an integral assembly 308 that includes the closure top) at a snap-lock joint 221. Above the snap-lock joint 221, leg 202 has a rotating coupling 240. One embodiment of rotating coupling 240 is depicted in FIG. 2B where the outer ring of bearing 260 is affixed to retractor leg 202, while the inner ring receives leg extension 219, such that leg extension 219 is free to rotate 360° about longitudinal axis 262.

Figure 2C:
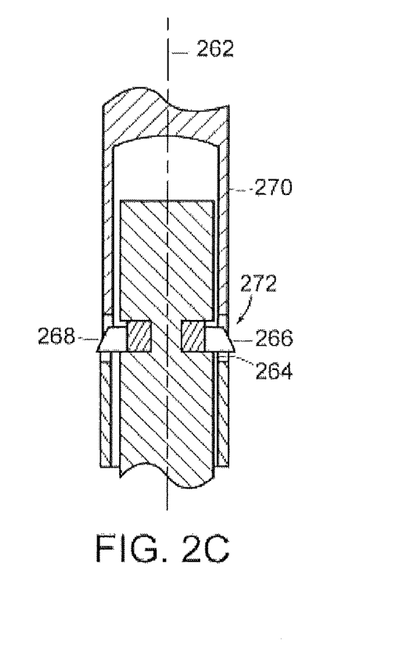
Figure 2D:
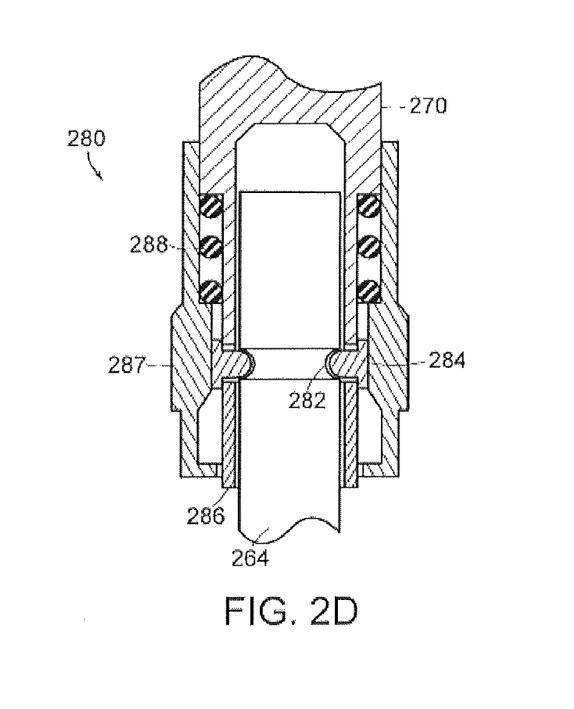
Figure 2E:
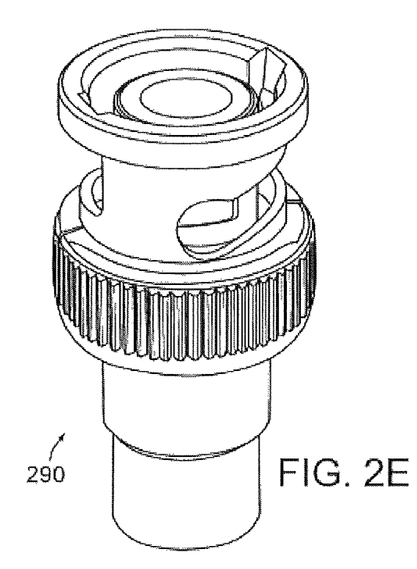
FIGS. 2E and 2F show two views of a twist-and-lock mechanism for coupling the rotatable leg extension to the closure screw, in accordance with certain embodiments of the present invention.
Figure 2F:
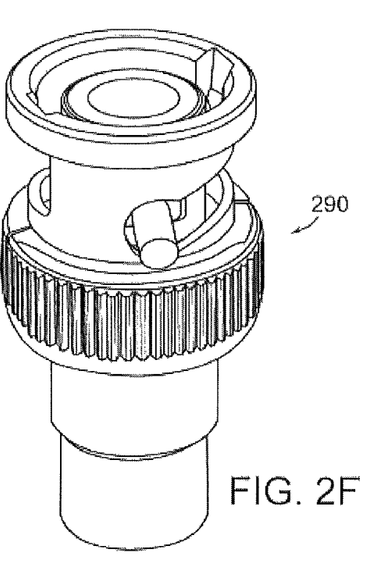
Figure 2H:
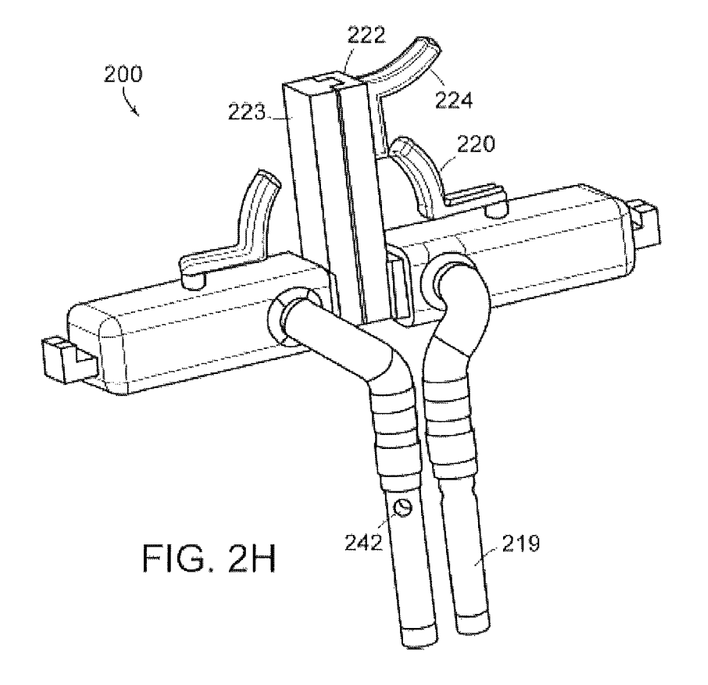
FIG. 2H is a perspective view of the base unit of FIG. 2A.
Figure 2I:
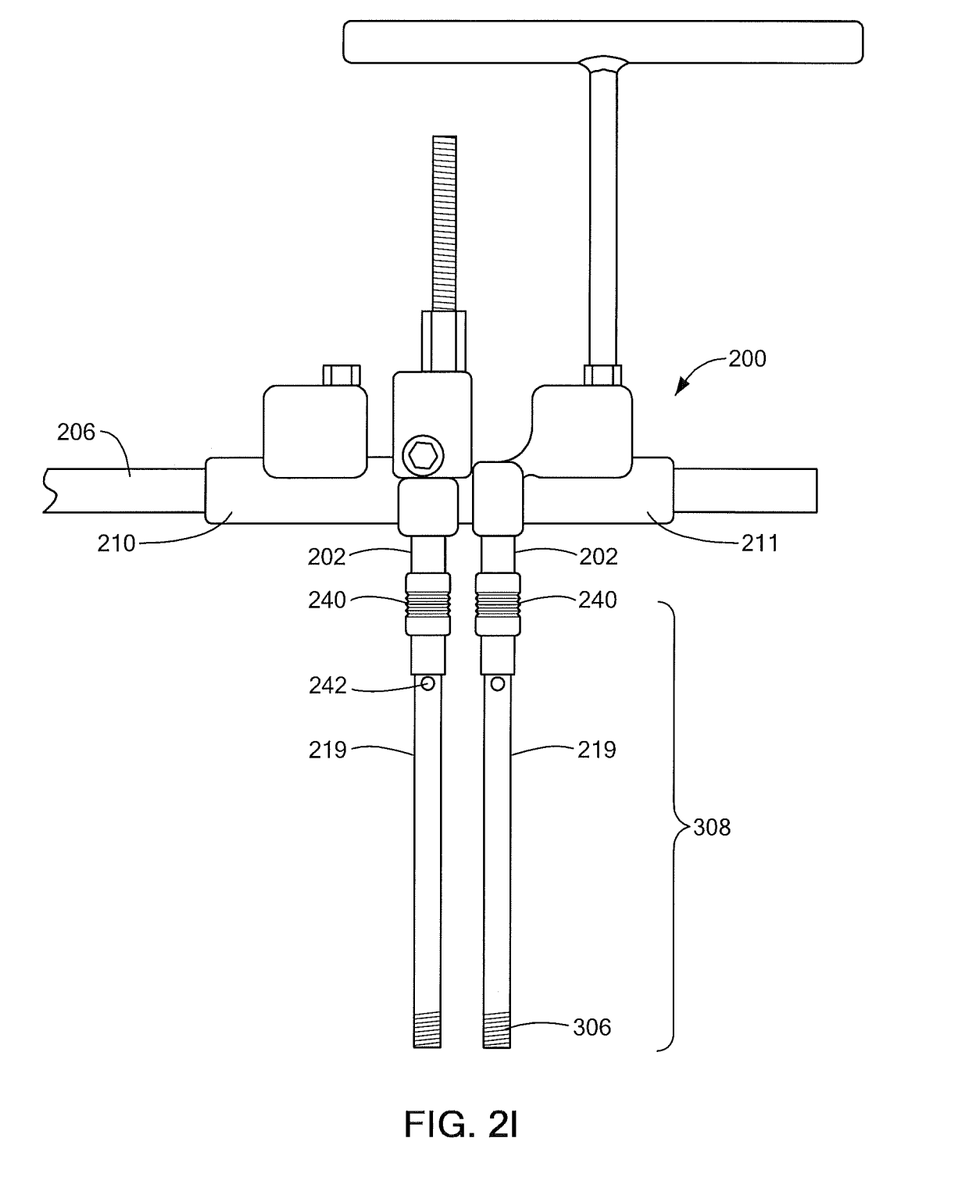
FIG. 2I illustrates a base unit, in accordance with an embodiment of the present invention.

An exemplary rotatable mechanism for engaging an upper leg 270 to a lower leg 264 is shown in FIG. 2C, where lower end 264 of the retractor leg (the lower end may be leg extension 219) contains two locking dogs 266, disposed 180° apart about axis 262, and having angled ends 268. The upper end 270 of retractor leg 202 has two opposed retaining slots 272 for receiving locking dogs 266 of the lower end 264. Locking dogs 266 are biased, by springs, for example, to engage slots 272 thereby maintaining contact between the upper and lower leg segments until the dogs are manually pushed out of retaining slots 272. Another exemplary mechanism for engaging upper leg 270 to lower leg 264 is the representative quick disconnect depicted in FIG. 2D and designated generally by numeral 280. Here, lower leg 264 contains a radial cut 282 that receives dogs 284 coupled to upper leg 270 when sleeve 286 is forced over the dogs by insertion of lower leg 264 into upper leg 270 forcing outer sleeve 287 against spring 288. Lower leg 264 is released by pushing outer sleeve 287 back against spring 288, allowing dogs 284 to release radial cut 282 in the lower leg 264. Quick-disconnect 280 may advantageously provide for free rotation of lower leg 264 with respect to upper leg 270. Other coupling modalities, such as the snap lock 290 depicted in FIGS. 2E and 2F are also within the scope of the present invention.

Figure 4:
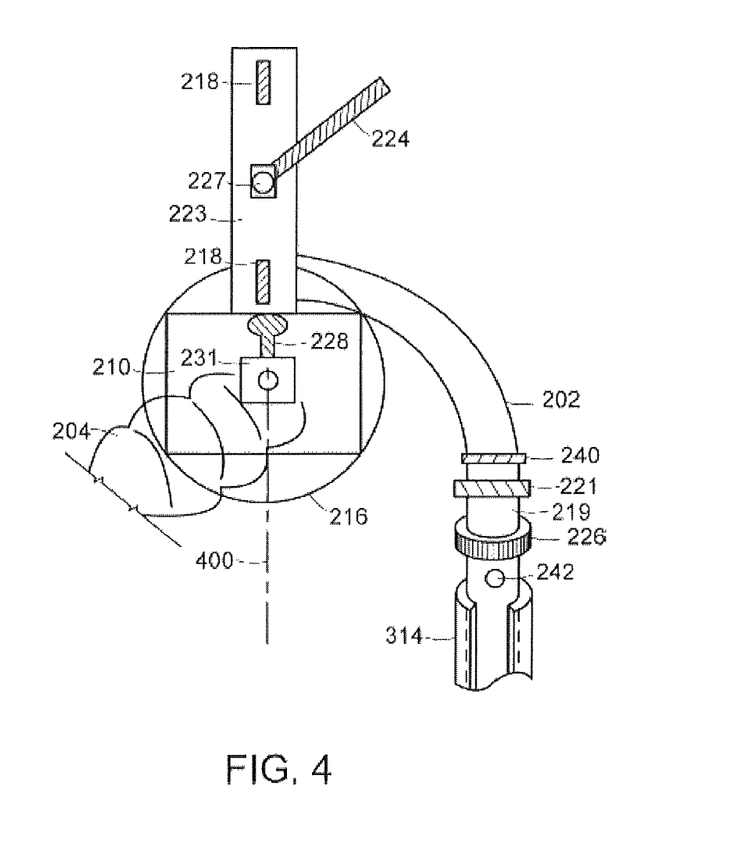
FIG. 4 shows a side view of the support trestle illustrating its coupling to a pedicle screw in accordance with an embodiment of the present invention.

Legs 202 may emanate as right cylinders directly from cross-bar sections 210 and 211, or, in accordance with other embodiments of the invention, may emanate in an arcuate manner, as depicted in FIG. 4 which shows retractor support structure 200 in cross-section as viewed from either the left or right side. While axis 254 (shown in FIG. 2A) of the cross-bar is oriented into the page in FIG. 4, wheel 216 is visible in FIG. 4, as is extender sleeve 314 of pedicle screw 300. The closure top threaded section 306 and extended shank 312 of the closure top are apparent as well. Wheels 214 and 216 are shown, whose purpose is for securing flexible aims 204 which hold each half of the retractor assembly 500, as shown in FIG. 5. Flexible arms 204 are locked to base unit 200 by screws 228 or other connectors.

In accordance with further embodiments of the invention, a flexible arm 204 extends from one or both sides of the retractor support structure and supports retractor 500, one embodiment of which is now described with reference to FIG. 5. Retractor 500 is shown in FIG. 5 as viewed from above. The retractor is supported, at the site of the surgery, by means of flexible arms 204 which couple it rigidly, but adjustably, to the retractor support structure described in the foregoing sections. Retractor 500 serves to retain spreaders 502 and 504 at a spacing prescribed by the surgeon to provide access to the region between vertebrae for excision of a disk or insertion of a graft. In an exemplary embodiment of the invention, the placement of pull pins 512 and 514 with respect to perforated spacing members 516 and 518 respectively, govern the coarse placement of the retractor in two orthogonal directions. Fine lateral adjustments of the position and opening of spreaders 502 and 504 is provided by ratchets 508 and 510.

The retractor support mechanism herein described may advantageously serve for procedures of posterior lumbar interbody fusion (PLIF) and transforaminal interbody fusion (TLIF). Its applicability, however, is not so limited and it may advantageously be applied in surgical circumstances where local support of a retractor relative to bone is desirable.

Moreover, the described embodiments of the invention are intended to be merely exemplary and numerous variations and modifications will be apparent to those skilled in the art. All such variations and modifications are intended to be within the scope of the present invention as defined in the appended claims.

What is claimed is:

1. An apparatus for exerting force on a bone with respect to a fulcrum, the apparatus comprising:
   a. a base structure, adapted for mechanical coupling to the fulcrum and exerting both transverse and axial force on the bone relative to the fulcrum with respect to a pedicle screw;
   b. a leg extension coupled to the base structure via a rotatable coupling, the leg extension, in turn, directly coupled to a closure top threaded for retention of a transverse rod in a corresponding helically-threaded head of a pedicle screw, the pedicle screw characterized by a pedicle screw axis and adapted for insertion into the bone;
   whereby rotation of the leg extension urges the closure top into the helically-threaded head of the pedicle screw in such a manner as to tighten the transverse rod with respect to the pedicle screw.

2. The apparatus of claim 1, wherein the base structure further comprises a simple machine adapted to urge the leg extension in both axial and transverse directions with respect to the pedicle screw axis.

3. The apparatus of claim 2, wherein the simple machine is adapted to urge the leg extension simultaneously in both axial and transverse directions with respect to the pedicle screw axis.

4. The apparatus of claim 2, wherein the simple machine is adapted to urge the leg extension sequentially in both axial and transverse directions with respect to the pedicle screw axis.

5. The apparatus of claim 2, wherein the simple machine is a toothed ratchet drive.

6. The apparatus of claim 2, wherein the simple machine is a worm drive.

7. The apparatus of claim 1, wherein the base structure further comprises at least one simple machine adapted to urge the leg extension in either axial and transverse directions with respect to the pedicle screw axis.

8. The apparatus of claim 1, wherein the leg extension and the closure top comprise an integral component.

9. The apparatus of claim 1, wherein the leg extension is frangibly coupled to the closure top.

10. The apparatus of claim 1, further comprising a retractor coupled to the base structure.

11. The apparatus of claim 10, further comprising a flexible arm for coupling the retractor to the base structure.

12. A leg extension for coupling a pedicle screw to a base structure from which both transverse and axial force may be applied through the pedicle screw to a bone, the leg extension characterized by a central axis and comprising:
   a. a first end adapted for rotatable coupling with respect to the base structure; and
   b. a second end threaded for retention of a transverse rod in a corresponding helically, threaded head of the pedicle screw.

13. The leg extension of claim 12, wherein the leg extension is integral with a closure top.

14. The leg extension of claim 13, wherein the leg extension and closure top are frangibly coupled.

15. The leg extension of claim 12, wherein the first end is further adapted for rotatable coupling to the base structure by means of a snap-lock joint.

16. The leg extension of claim 12, further comprising a through-hole transverse to the central axis of the leg extension for receiving a torque pin for application of torque about the central axis.

* * * * *